US 6,663,853 B2

(12) United States Patent
Singh

(10) Patent No.: US 6,663,853 B2
(45) Date of Patent: Dec. 16, 2003

(54) LIP CARE MOISTURIZER

(75) Inventor: Mohinder Singh, Naperville, IL (US)

(73) Assignee: Blistex Inc., Oak Brook, IL (US)

( * ) Notice: Subject to any disclaimer, the term of this patent is extended or adjusted under 35 U.S.C. 154(b) by 0 days.

(21) Appl. No.: 09/727,277

(22) Filed: Nov. 30, 2000

(65) Prior Publication Data

US 2002/0098158 A1 Jul. 25, 2002

(51) Int. Cl.[7] .......................... A61K 7/025; A61K 6/00; A61K 7/42; A61K 31/74; A01N 59/16
(52) U.S. Cl. ..................... 424/64; 424/401; 424/59; 424/78.02; 424/660; 514/937; 514/938
(58) Field of Search ................... 424/59, 63, 64, 424/401, 60, 400, 78.02, 78.03, 600, 658, 660, 641, 642; 514/844, 937, 938

(56) References Cited

U.S. PATENT DOCUMENTS

| | | | | |
|---|---|---|---|---|
| 3,914,131 A | * | 10/1975 | Hutchison | 106/268 |
| 4,323,694 A | * | 4/1982 | Scala, Jr. | 560/103 |
| 5,085,856 A | * | 2/1992 | Dunphy et al. | 424/64 |
| 5,637,291 A | * | 6/1997 | Bara et al. | 424/59 |
| 5,690,918 A | * | 11/1997 | Jacks et al. | 424/64 |
| 5,783,601 A | * | 7/1998 | Tanahashi et al. | 514/557 |
| 5,804,168 A | * | 9/1998 | Murad | 424/59 |
| 5,885,558 A | * | 3/1999 | Stanzl et al. | 424/59 |
| 5,932,196 A | * | 8/1999 | Motley et al. | 424/62 |

FOREIGN PATENT DOCUMENTS

WO    93/11742    * 6/1993

* cited by examiner

*Primary Examiner*—Michael G. Hartley
*Assistant Examiner*—Sharmila S Gollamudi

(57) ABSTRACT

A lip care moisturizing product in the form of a water-in-oil emulsion, containing at least one fatty acid ester, at least one wax, the total of said at least one fatty acid ester and said at least one wax being at least about 1.0%, liposomes containing water therein, and an emulsifier. The emulsifier is preferably a mixture of behenoyl stearate and sodium borate, and the liposomes preferably contain a mixture of water and glycerin.

17 Claims, No Drawings

LIP CARE MOISTURIZER

BACKGROUND OF THE INVENTION

The invention relates to the field of lip care products, including lipsticks and lip balms with penetrating ingredients.

Lipsticks have been used for many years to alter appearance of the lips and the facial characteristics of the wearer. For example, narrow lips may be widened and broad lips narrowed. Besides altering the shape of the lips, lipsticks can be made in a great number of colors and shades according to fashion and the mood of the wearer.

Lipsticks are most often based on waxy and oily materials, which give the lips an oily and shining look, but a greasy feel. Among such lipophilic materials are hydrocarbon oils, fatty acid esters, waxes, fatty alcohols and mixtures thereof. Lipsticks may also contain other emollients which provide a supple and pleasant feeling to the lips of the wearer. It has also been proposed to include a small amount of water in some lipsticks for moisturizing the lips, the water being emulsified in the waxy material by the use of various emulsifiers and polymers. However, water containing lipsticks have been found to be deficient in terms of storage stability; in particular, with a semi-open package, it is difficult to retain the moisture intact. Moreover, the water content of such products has often been undetectable to the user. Thus, female consumers still favor anhydrous colored lipsticks.

Lip balms are similar to lipsticks and have long been used to protect lips from the effects of the environment, such as sunlight, wind, and cold. Lip balms are generally occlusive compositions which may contain a variety of lipophilic materials such as fats, oils, waxes and emollients which soften lips and protect against the effects of wind. Both lipsticks and lip balms may contain sunscreens which block damaging radiation from the sun and other ingredients for imparting fragrance, and physical characteristics.

SUMMARY OF THE INVENTION

It is therefore an object of the invention to provide a lip moisturizing product with a stable water content over time.

It is a further object of the invention to provide a lip moisturizing product containing moisturizers which penetrate into the skin.

To achieve these and other objects, the invention is directed to a lip care moisturizing product in the form of a water in oil emulsion in which the water content is in the form of liposomes containing water and glycerin, the liposomes being dispersed in the oily/waxy phase by an emulsifier system preferably based on behenoyl stearate and sodium borate (borax).

DETAILED DESCRIPTION OF THE INVENTION

As used herein the term "lip care moisturizing product" refers to lipsticks, lip balms, and other products used to treat the lips whether in solid or pasty form. The lip care products of the invention are based on the use of liposomes, which are defined generally as spherical, closed bilayer structures formed by hydrating lipids or lipid-like amphiphilic materials under appropriate conditions. Liposomes may be differentiated based on lamellarity, size, and function. Small unilamellar vesicles (SUV's) have a size between 25 and 75 nm, while large unilamellar vesicles (LUV's) have a size greater than 100 nm. Unilamellar liposomes that are sterically stabilized by incorporating proteins are known as "stealth liposomes" while liposomes containing cationic lipids carry a net positive charge and are known as cationic liposomes. Liposomes may also contain lipids designed to bind to specific cells or proteins, and these are known as targeted liposomes.

Various methods are known for producing liposomes.

In a first method, a solution of lipid is dried in a high vacuum to remove all organic solvent, then hydrated in an appropriate buffer to produce a raw liposome dispersion, which is generally a mixture of univesicular and unilamellar liposomes. The dispersion can be forced through a membrane to obtain large unilamellar vesicles, with size depending on the pore size of the membrane. Alternatively, the raw dispersion can be treated by sonication to obtain small unilamellar vesicles, which are harvested by ultracentrifugation.

A mixture of large and small unilamellar liposomes can be prepared by dissolving dry lipids in aqueous media in the presence of a detergent, then removing the detergent by dialysis.

Industrially, liposomes can be obtained by forming a slurry of lipid in water and microfluidizing at 12,000–14,000 PSI. This process can be performed continuously to produce unilamellar liposomes and no organic solvent is necessary.

A particularly preferred liposome for the products of the invention is sold as Liposomes FG™ by The Collaborative Group, Ltd. of East Setauket, N.Y. These liposomes are formed of lecithin as the lipid and contain a mixture of water and glycerin.

The compositions of the invention comprise a stable emulsion base containing about 1.0 to 35.0% by weight purified water, and about 0.2% to 30% by weight liposome dispersion containing a purified water-glycerin mixture. In one embodiment, the liposome dispersion contains 82% by weight liposomes and 18% by weight of a water-glycerin mixture. The liposomes are preferably in the size range of about 25 to 75 nm.

The emulsion base also preferably contains 0.05 to 20% by weight, and preferably less than 5% by weight, of a gelling agent, i.e. cholestryl/behenyl/octyldodecyl lauroyl glutamate, which will absorb and retain water in an amount of 4% to 300% of its own weight.

The compositions of the invention typically contain a mixture of esters and waxes as the base material, although the particular esters and waxes used are not critical. Typical esters used in such products include jojoba esters, dioctyl adipate, octyl stearate, octyl palmitate and caprylic/capric triglycerides. Esters are typically present in a total amount of about 0.5 to 35% by weight, preferably about 5 to 35% by weight.

Typical waxes used are ozokerite (ceresin), microcrystalline waxes and petrolatum, in a total amount of about 0.5 to 29% by weight, preferably about 3 to 29% by weight.

The total amount of esters and waxes will affect the physical form of the product. Thus, pasty products will generally have between about 1 and 25% by weight total esters and waxes, whereas solid products like lipsticks and lip balms will generally have between about 5 and 35% by weight total esters and waxes.

Sunscreens which may be used include octylmethoxycinnamate and benzophenone-3, in amounts necessary to achieve sun protection factor (SPF) 15. The total amount of sunscreen in the composition is generally in the range of 5.0 to 30% by weight, preferably 7.0 to 15% by weight.

The compositions preferably contain one or more penetrating moisturizers, particularly squalane and panthenol in a total amount of about 0.5 to 5% by weight.

The water in oil emulsions of the invention are typically produced using stearate emulsifiers, for example glyceryl stearate, PEG stearate and behenoyl stearate. Behenoyl stearate emulsifier is very effective in emulsifying 33–55% by weight water into 45–67% by weight of non-polar oils. The best results are obtained by dissolving about 2–7.5% by weight emulsifier in the oil phase, and buffering the system by dissolving up to 4% by weight borax in the water phase.

A typical composition according to the invention thus contains, by weight:

| | |
|---|---|
| esters | up to 35% |
| waxes | up to 29% |
| sunscreens | 7.0–15% |
| emulsifier | up to 7.5% |
| liposomes and other ingredients | to 100%. |

A preferred composition also contains a skin protectant, and has the following composition, by weight:

| | |
|---|---|
| sunscreen and skin protectants | 12% |
| esters | 31% |
| emulsifier | 2.5% |
| gelling agent | 0.5% |
| waxes | 29% |
| moisturizer | 2% |
| purified water and liposomes | 18% |
| preservatives and flavors | 5% |

The composition is prepared by mixing the waxes and esters and melting together to form an oil phase. The purified water is blended with cholestryl/behenyl/octyldodecyl lauroyl glutamate and passed through a high shear inline micronizer to form a water phase. The oil phase and the water phase are mixed together and passed through a high shear micronizer to obtain a water in oil emulsion. Preblending of the water phase is important to stabilize the emulsion without loss of moisture during further processing.

After obtaining the emulsion, liposomes are purged into the system at a rate of 1 liter per hour at a temperature below 45° C. while mixing at less than 400 RPM. Because liposomes are delicate, excessive heat and shearing are to be avoided in the mixing step.

EXAMPLE

A lip balm is prepared with the following composition (by weight):

| | |
|---|---|
| Active ingredients: | |
| octyl methoxycinnamate | 7.500% |
| benzophenone | 2.500% |
| dimethicone | 2.000% |
| Other ingredients: | |
| dioctyl adipate/octyl stearate/octyl palmitate | 15.244% |
| caprylic/capric triglycerides | 13.596% |
| microcrystalline wax | 11.712% |

-continued

| | |
|---|---|
| liposome composition | 10.560% |
| petrolatum | 9.024% |
| ozokerite | 7.680% |
| purified water | 6.680% |
| flavor | 4.000% |
| jojoba esters | 2.400% |
| behenoyl stearate | 2.400% |
| sodium borate | 1.360% |
| panthenol | 1.000% |
| squalane | 1.000% |
| cholesteryl/behenyl/octadecyl lauroyl glutamate | 0.480% |
| methyl paraben | 0.288% |
| propyl paraben | 0.288% |
| ethyl paraben | 0.096% |
| butyl paraben | 0.096% |
| sodium saccharin | 0.096% |
| TOTAL: | 100.000% |

What is claimed is:

1. A lip care moisturizing product in the form of a water-in-oil emulsion having an oily phase and an aqueous phase, said product comprising, by weight:
   about 0.5 to 35% of at least one fatty acid ester;
   about 0.5 to 29% of at least one hydrocarbon wax;
   the total of said at least one fatty acid ester and said at least one hydrocarbon wax being at least about 1.0%;
   about 0.2 to 30% of liposomes; and
   about 1 to 7% of an emulsifier system consisting essentially of behenoyl stearate in combination with sodium borate,
   said oily phase comprising said at least one fatty acid ester, said at least one wax, and said emulsifier.

2. A product according to claim 1, wherein said liposomes contain a mixture water and glycerin.

3. A product according to claim 1, additionally comprising 5 to 30% of at least one sunscreen.

4. A product according to claim 3, wherein the at least one sunscreen is selected from the group consisting of octyl methoxycinnamate and benzophenone-3.

5. A product according to claim 3, wherein the at least one sunscreen is present in an amount sufficient that the product has a sun protection factor of at least 15.

6. A product according to claim 1, additionally comprising about 1 to 7% of at least one moisturizing agent.

7. A product according to claim 6, wherein the at least one moisturizing agent is selected from the group consisting of squalane and panthenol.

8. A product according to claim 1, wherein the product contains water in an amount of about 1–35% by weight.

9. A product according to claim 1, wherein said liposomes have a particle size of about 25 to 75 nm.

10. A product according to claim 1, wherein said at least one fatty acid ester is selected from the group consisting of dioctyl adipate, octyl stearate, octyl palmitate, jojoba esters, caprylic triglycerides and capric triglycerides.

11. A product according to claim 1, wherein said at least one wax is selected from the group consisting of petrolatum, microcrystalline wax and ozokerite.

12. A product according to claim 1, additionally comprising about 0.05 to 20% of a water gelling agent.

13. A product according to claim 12, wherein said water gelling agent is selected from the group consisting of cholestryl lauroyl glutamate, behenyl lauroyl glutamate, octyldodecyl lauroyl glutamate, and mixtures thereof.

14. A product according to claim 1, which is a substantially solid lipstick or lip balm containing about 5 to 35% total of said at least one fatty acid ester and said at least one wax.

15. A product according to claim 1, which is a pasty product containing about 0.5 to 25% total of said at least one fatty acid ester and said at least one wax.

16. A product according to claim 1, comprising, by weight:

said at least one ester up to 35%

| | |
|---|---|
| said at least one ester | up to 35% |
| said at least one wax | up to 29% |
| sunscreen | 7.0 to 15% |
| emulsifier | up to 7.5% |
| liposomes | 1.0 to 30%. |

17. A product according to claim 1, comprising, by weight:

| | |
|---|---|
| sunscreen and skin protectants | 12% |
| esters | 31% |
| emulsifier | 2.5% |
| gelling agent | 0.5% |
| waxes | 29% |
| moisturizer | 2% |
| purified water and liposomes | 18% |
| preservatives and flavors | 5%. |

\* \* \* \* \*